United States Patent [19]
Thompson et al.

[11] Patent Number: 5,814,982
[45] Date of Patent: Sep. 29, 1998

[54] COUPON TEST STATION FOR MONITORING THE EFFECTIVENESS OF CATHODIC PROTECTION

[75] Inventors: Neil G. Thompson, Dublin; Kurt M. Lawson, Sugar Grove, both of Ohio

[73] Assignee: CC Technologies Systems, Inc., Dublin, Ohio

[21] Appl. No.: 887,498

[22] Filed: Jul. 2, 1997

[51] Int. Cl.⁶ .................................................. G01N 27/42
[52] U.S. Cl. .......................... 324/71.1; 324/425; 204/404
[58] Field of Search ................................... 324/425, 71.1, 324/71.2, 693, 700, 713; 204/404; 205/775.5, 776.5; 73/86

[56] References Cited

U.S. PATENT DOCUMENTS

| | | | |
|---|---|---|---|
| 3,769,521 | 10/1973 | Caldwell et al. | 307/95 |
| 3,893,026 | 7/1975 | Glazkov et al. | 204/404 |
| 4,060,461 | 11/1977 | Seyl | 324/71.2 |
| 4,179,920 | 12/1979 | Schuller et al. | 204/404 |
| 4,409,080 | 10/1983 | Slough | 204/404 |
| 4,823,072 | 4/1989 | Walcott et al. | 166/113 |
| 4,839,580 | 6/1989 | Moore et al. | 324/700 |
| 4,928,760 | 5/1990 | Freitas | 73/86 |
| 5,087,876 | 2/1992 | Murphy et al. | 324/71.2 |
| 5,144,247 | 9/1992 | Speck | 324/71.1 |
| 5,216,370 | 6/1993 | Bushman et al. | 324/71.1 |
| 5,469,048 | 11/1995 | Donohue | 324/71.1 |

OTHER PUBLICATIONS

Frank A. Perry, "A Review Of Stray Current Effects On A Gas Transmission Main In The Boston, Massachusetts Area", *Nace International Annual Conference And Corrosion Show—Corrosion 94,* Paper No. 590, pp. 1–13 (month unavailable).

Martin et al., "A Method For Determining Pipeline Polarised Potentials In Stray Current Areas Using Linear Regression Analysis", *Industrial Corrosion,* vol. 3, No. 3, May 1985, pp. 10–14.

Ronald C. Robinson, "Computerized Corrosion Monitoring For Metallic Pipeline Structures", *Materials Performance,* vol. 74, Feb. 1993, pp. 30–34.

B. A. Martin, "Cathodic Protection The Ohmic Component Of Potential Measurement Laboratory Determinations With A Polarization Probe In Aqueous Environments", *Materials Performance,* vol. 69, Jan. 1981, pp. 52–57.

Cott Manufacturing Company, 1944 Gardena Avenue, Glendale, California 91204, "Finkprobe Integrated Steel Coupon Test Station" brochure (month available).

Cott Manufacturing Company, 1944 Gardena Avenue, Glendale, California 91204, "Big Fink Cathodic Protection Test Station" brochure (month unavailable).

*Primary Examiner*—Diep N. Do
*Attorney, Agent, or Firm*—Frank H. Foster; Kremblas, Foster, Millard & Pollick

[57] ABSTRACT

A test station for measuring the effectiveness of cathodic protection including a cylindrical plastic reference tube extending downwardly through the soil to near the protected structure, such as a pipe. Two plastic coupon tubes extend within the chamber of the reference tube attaching to opposite sides of its interior sidewalls. First and second circular cylindrical rod-shaped coupons attach to, and sealingly engage, the bottom ends of the coupon tubes. Insulated conductors extend from attachment to each coupon upwardly through the coupon tubes. A first coupon is electrically connected to the pipe, and the second coupon is used to measure a free-corrosion (native) potential.

13 Claims, 13 Drawing Sheets

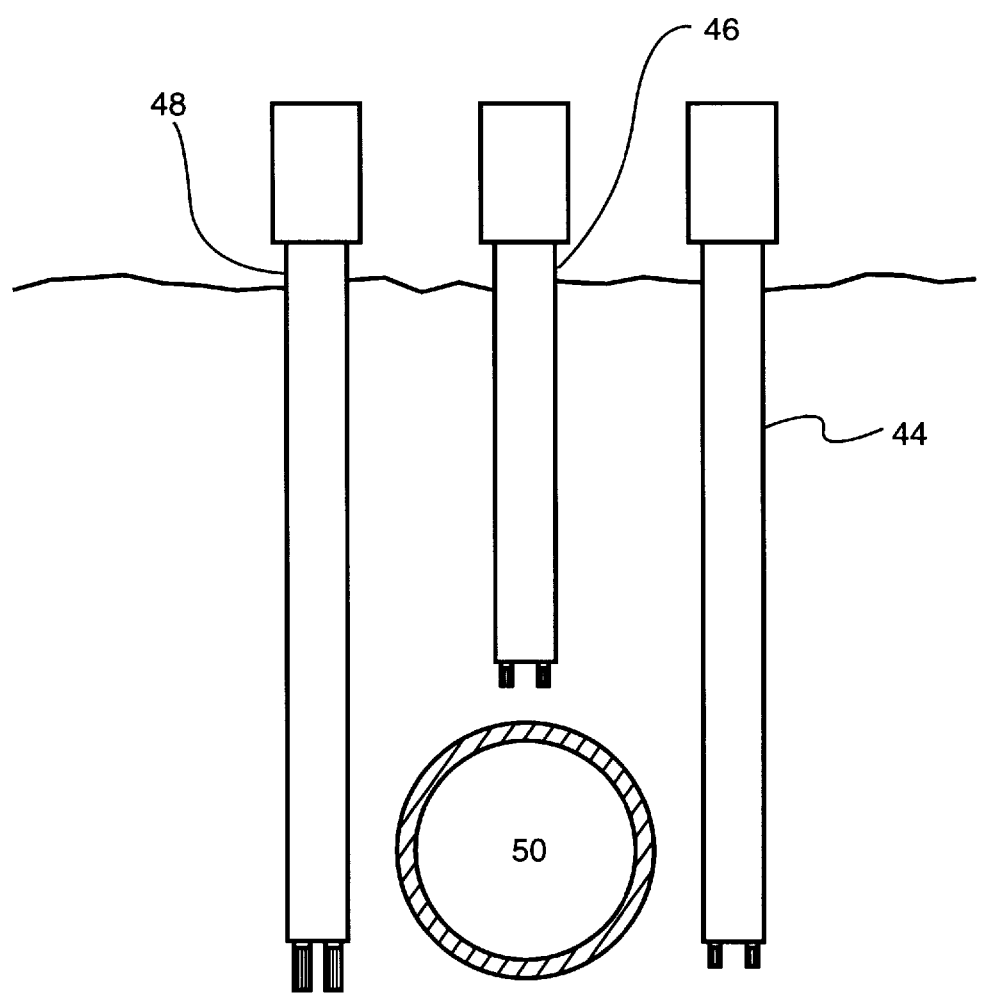

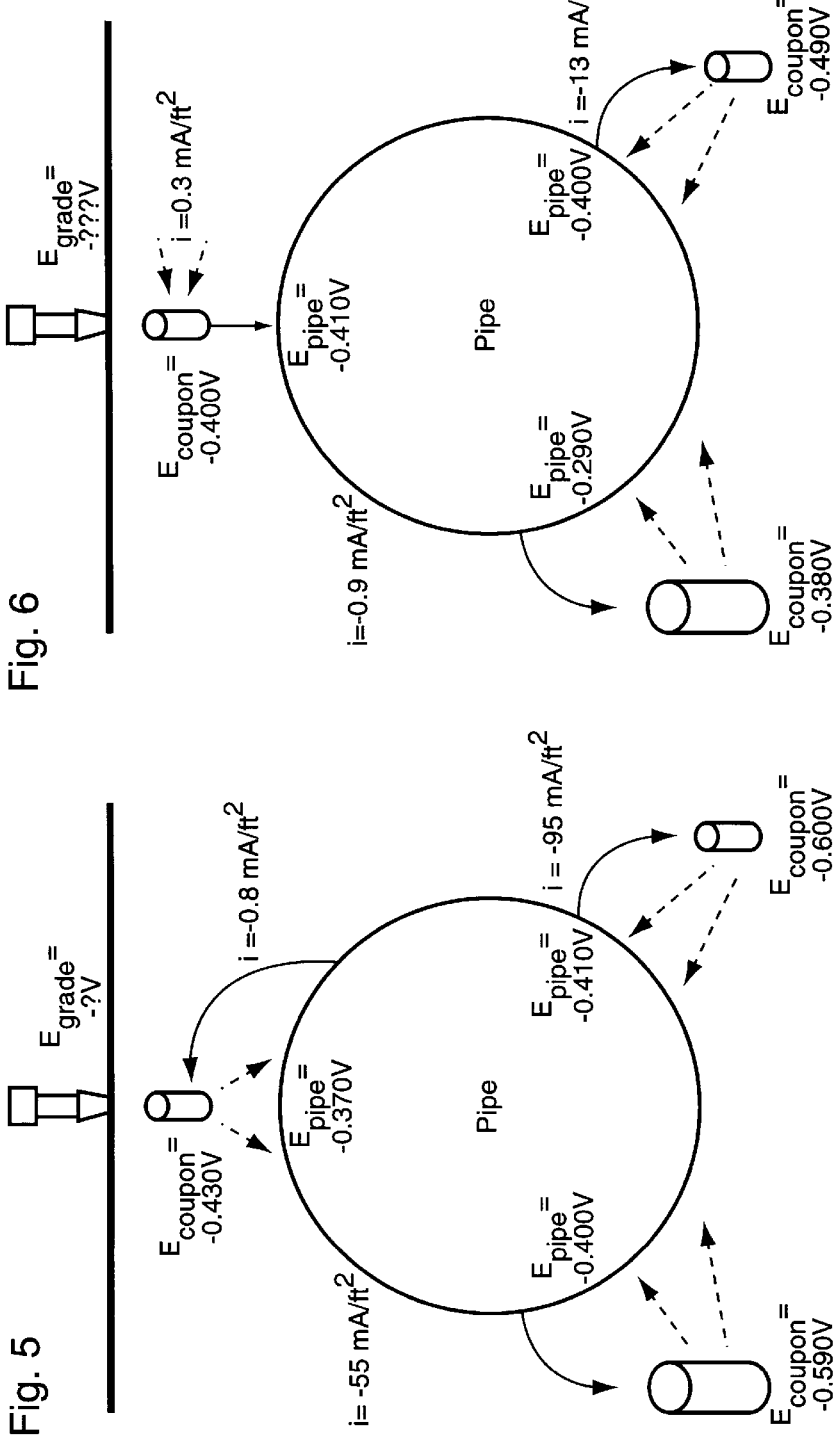

Location 39.25 at Victorville, CA
(prior to anode bed upgrade)

Location 32.68 at Victorville, CA
(prior to anode bed upgrade)

Summary Of Victorville, California Field Site Data (Off-Potentials And Coupon Currents) For The November 2, 1994 Field Site Evaluation, Prior To Anode Bed Upgrade.

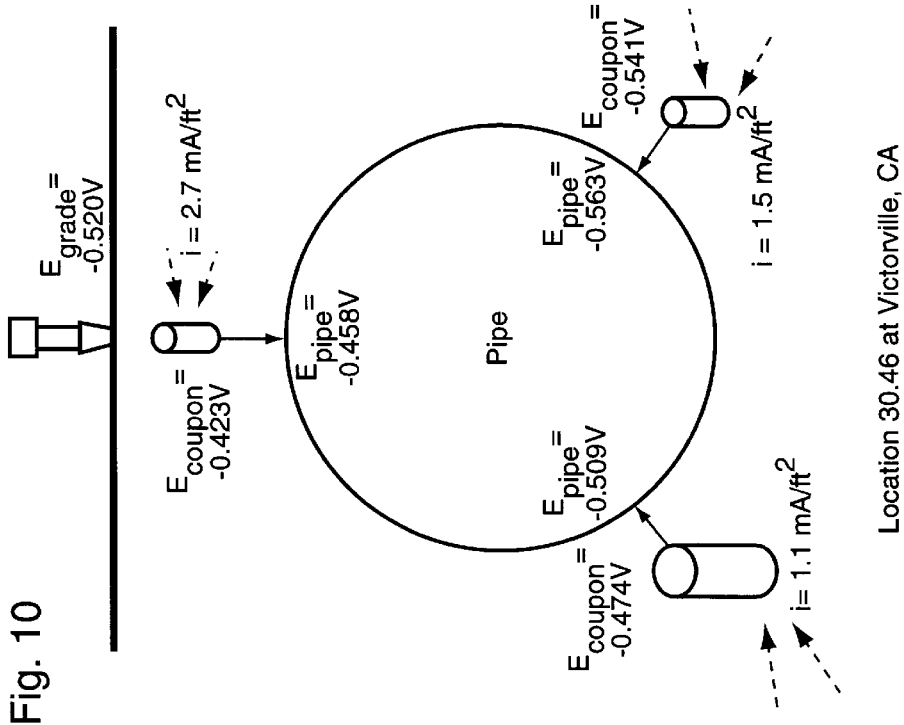
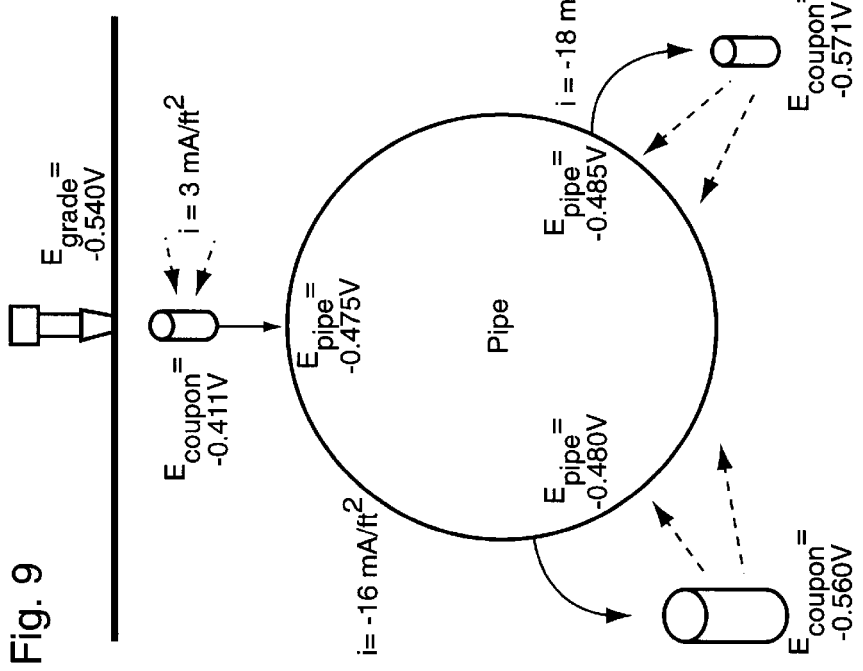

Location 39.25 at Victorville, CA

Location 32.68 at Victorville, CA

Summary Of Victorville, CA Field Site Data (Off-Potentials And Coupon Currents) For May 4, 1995 Field Evaluation.

Summary Of Elkins, WV Field Site Data (Off-Potentials And Coupon Currents) For The May 31, 1995 Field Site Evaluation.

Summary Of Elkins, WV Field Site Data (Off-Potentials And Coupon Currents) For The May 31, 1995 Field Site Evaluation.

Top Standard Coupon Location 2

Top Standard Coupon Location 1

Bottom Large Coupon Location 2

Comparison Of Coupon Versus Pipe Potentials As A Function Of CP Level For Coupons Located On Poorly Coated Pipe Section.

Bottom Large Coupon Location 1

Bottom Standard Coupon Location 2

Bottom Standard Coupon Location 1

Comparison Of Coupon Versus Pipe Potentials As A Function Of CP Level For Coupons Located On Poorly Coated Pipe Section.

Top Standard Coupon Location 2

Top Standard Coupon Location 1

Bottom Large Coupon Location 2

Comparison Of Coupon Versus Pipe Potentials As A Function Of CP Level For Coupons Located On Well Coated Pipe Section.

Bottom Large Coupon Location 1

Bottom Standard Coupon Location 2

Bottom Standard Coupon Location 1

Comparison Of Coupon Versus Pipe Potentials As A Function Of CP Level For Coupons Located On Well Coated Pipe Section.

COUPON TEST STATION FOR MONITORING THE EFFECTIVENESS OF CATHODIC PROTECTION

TECHNICAL FIELD

The invention relates to a test station for monitoring the effectiveness of cathodic protection applied to a structure immersed in an electrolyte (e.g. a buried pipe, tank, piling, steel encased in concrete, pier or other structure in natural water or marine environment.

BACKGROUND ART

Buried or immersed metal structures, such as pipes and tanks, are exposed to an electrochemical corrosion process in the underground environment. The metal structure becomes an electrode and the soil an electrolyte so that an electrolytic cell is formed causing the corrosion of the buried structure.

Some corrosion arises from naturally occurring processes at specific locations on the buried structure involving electrical current flow into the ambient soil electrolyte from sites acting as anodes via the corrosion reaction. The current flows to sites on the structure acting as cathodes where reduction reactions occur. The corrosion is often additionally caused or accelerated by voltages applied to a local region of the pipe by manmade structures, including local transit systems, power distribution systems, and industrial plants.

Cathodic protection has been employed to mitigate the electrochemical corrosion reaction on the structure. It is possible to cathodically protect a structure by an appropriate galvanic coupling to create a sacrificial anode, or an external power supply that generates an impressed current through the soil from an anode to the protected object (using conventional current flow direction).

With a cathodic protection system, industry accepted criteria involve the measurement of the electrochemical potential of the structure to establish the level of cathodic protection sufficient to mitigate corrosion of the buried metal structure. The ordinary practice to determine the necessary level of cathodic protection is to measure the potential difference between the buried structure, which is an electrode, and a reference electrode placed, at grade, in contact with the soil, which is an electrolyte. However, when this measurement is taken while the cathodic protection system is operating, a voltage drop through the soil due to the cathodic protection current, referred to as the IR (voltage) drop, causes an error in the potential measurement.

In order to measure a potential that is free of IR drop, it is common to measure the potential immediately following interruption of the cathodic protection current. The instantaneous voltage drop which occurs immediately after the cathodic protection is turned off is equal to the IR drop caused by the interrupted cathodic protection current. Because the electrochemical interface of the protected structure has a capacitive component, the potential of that interface does not change immediately following interruption as does the IR drop. Therefore, the potential measured immediately following interruption of the cathodic protection current, when current, I, is zero, is the potential of the protected structure free of IR drop. This potential is referred to as off-potential.

Problems arise in interrupting the cathodic protection. Extremely long buried pipelines have multiple cathodic protection stations, all of which must be interrupted simultaneously, or interrupted using a non-synchronous method in which all of the IR drops are summed. The galvanic cathodic protection systems are not designed to be interrupted because the anodes are typically directly connected to the protected structure. Additionally, second-party cathodic protection systems that are either unknown or cannot be interrupted may be present in the area. Other problems exist, such as stray current effects, (from power distribution systems, dc transit systems, telluric effects, etc.) which are not interruptable, and rapid IR transients, which immediately follow interruption.

In order to avoid the problems associated with interruption of the entire cathodic protection system, coupons are used to monitor the level of cathodic protection on buried metal structures such as pipes. The coupon is a bare metal sample having substantially the same metallurgical attributes as the pipe. The coupon is placed in the soil near the pipe and connected to the pipe. Therefore, the coupon sees the same cathodic protection current source as the pipe. The connection between the pipe and the coupon is interrupted for a time period, during which time the potential difference between the coupon and a reference electrode is measured. The pipe's cathodic protection is never interrupted, since only the pipe-to-coupon connection is interrupted. The coupon's potential simulates the potential of a pipe coating defect of a similar surface area as the coupon. The coupon's potential can be measured without interrupting the cathodic protection to the pipe, and therefore without some of the problems inherent in interrupting the entire cathodic protection system. In addition, once the coupon is interrupted, it is an isolated, small, piece of metal in the soil and stray currents are eliminated from its surface. In contrast, stray currents are generally not eliminated from a pipeline upon interruption of the entire cathodic protection system.

Several technical articles have been written about the field of cathodic protection. These include Frank A. Perry, "A Review Of Stray Current Effects On A Gas Transmission Main In The Boston, Massachusetts Area", *NACE International Annual Conference And Corrosion—Show Corrosion 94*, Paper No. 590, pp. 1–13; Martin et al., "A Method For Determining Pipeline Polarised Potentials In Stray Current Areas Using Linear Regression Analysis", *Industrial Corrosion*, Vol. 3, No. 3, May 1985, pp. 10–14; Ronald C. Robinson, "Computerized Corrosion Monitoring For Metallic Pipeline Structures", *Materials Performance*, Vol. 74, February 1993, pp. 30–34; B. A. Martin, "Cathodic Protection The Ohmic Component Of Potential Measurement Laboratory Determinations With A Polarization Probe In Aqueous Environments", *Materials Performance*, Vol. 69, January 1981, pp. 52–57.

Additionally, several patents teach cathodic protection devices. Donohue, in U.S. Pat. No. 5,469,048 shows a cathodic protection measurement apparatus using a coupon mounted to a primary tube placed in the soil near a buried pipe. A secondary tube is attached to the exterior of the primary tube, and a reference electrode is positioned at the bottom of the secondary tube near the coupon. Other methods and devices for use in association with cathodic protection apparatuses are shown in U.S. Pat. No. 4,823,072 to Walcott et al., U.S. Pat. No. 4,179,920 to Schuller et al., U.S. Pat. No. 4,928,760 to Freitas. Furthermore, Cott Manufacturing Company (1944 Gardena Avenue, Glendale, Calif. 91204) manufactures a device marketed under the trademark FINKPROBE which uses coupons to test cathodic protection. Cott Manufacturing Company also makes a product marketed under the trademark BIG FINK which is a "terminal for monitoring electric currents and potentials."

Despite the existence of a significant number of devices for determining the effectiveness of cathodic protection, the need exists for a simple, inexpensive and accurate measuring device.

BRIEF DISCLOSURE OF INVENTION

The invention is a test station for measuring the effectiveness of cathodic protection for mitigating the corrosion of a buried metal structure. The test station comprises a nonconductive reference tube having a sidewall surrounding and defining an interior, elongated chamber. A first coupon of substantially the same metal as the buried structure is mounted to, and protrudes out of, a first reference tube end. The first coupon has an attached electrically insulated conductor extending from the coupon, through the reference tube for connecting to the buried metal structure. A second coupon of substantially the same metal as the buried structure is also mounted to, and protrudes out of, the first reference tube end. The second coupon has an attached electrically insulated conductor extending from the coupon through the reference tube.

It is contemplated that first and second spaced, coupon tubes are mounted to the opposite, interior sidewalls of the reference tube within the reference tube chamber. Each coupon tube has a sidewall terminating in a tube end near the first, lower end of the reference tube. The first coupon is mounted to the end of the first coupon tube and the second coupon is mounted to the end of the second coupon tube. The coupon tubes are mounted to the sidewall of the reference tube at 180 degree intervals from each other, and both mounted coupons protrude the same distance out of the lower end of the reference tube. This distance is preferably minimal, such as ¼ to ½ inch. In use, the reference tube is buried in the soil, the chamber is filled with soil up to grade and a reference electrode is positioned within the chamber of the reference tube in contact with the soil.

BRIEF DESCRIPTION OF DRAWINGS

FIG. 4 is a side view illustrating three possible coupon test station positions relative to a pipe.

FIGS. 5 through 16 illustrate diagrammatically the data from two of the experimental field sites.

Figure 1:
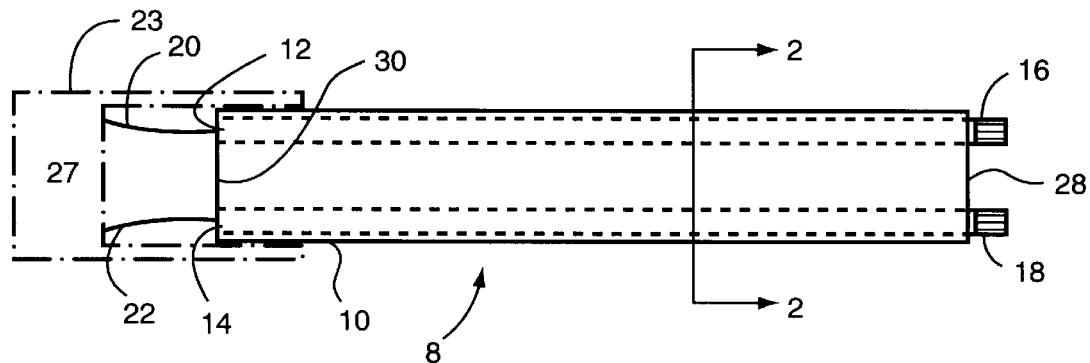
FIG. 1 is a side view illustrating the preferred embodiment of the present invention.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected or terms similar thereto are often used. They are not limited to direct connection but include connection through other circuit elements where such connection is recognized as being equivalent by those skilled in the art. In addition, many electronic devices are illustrated which are of a type which perform well known operations on electronic signals. Those skilled in the art will recognize that there are many, and in the future may be additional, alternative devices which are recognized as equivalent because they provide the same operations on the signals.

DETAILED DESCRIPTION

Figure 2:
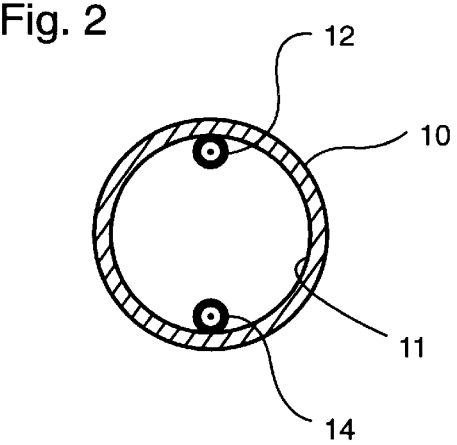
FIG. 2 is an end view in section through the line 2—2 of FIG. 1.

The preferred test station 8 is shown in FIGS. 1 and 2 including a reference tube 10, which is preferably a 3 inch pipe made of plastic, such as polyethylene, polyvinylchloride, polycarbonate, etc. The reference tube 10 has an elongated interior chamber bounded by the sidewall 11. A pair of electrical conduits, such as plastic coupon tubes 12 and 14 which are preferably made of plastic, are mounted within the chamber of the reference tube 10, attached to the sidewall 11 by an adhesive, a weld or some other conventional fastener. The coupon tubes 12 and 14 are attached to opposite sides of the interior surface of the sidewall 11, positioned at 180 degree intervals from each other, as is apparent from FIG. 2. The coupons attached to the lower ends of the coupon tubes 12 and 14 protrude about 0.5 inches or less from the first end 28 of the reference tube 10. The opposite ends of the coupon tubes 12 and 14 are flush with the second, opposite reference tube end 30. If the attachment between the coupon tubes 12 and 14 and the reference tube sidewall 11 fails, this will be apparent because the top end of one or both of the coupon tubes will no longer be flush with the reference tube end 30.

The reference tube 10 and the coupon tubes 12 and 14 are preferably circular cylindrical tubes. A cylinder is defined as the surface traced by a straight line which stays parallel to a fixed straight line while it moves along a path and intersects a fixed curve. A circular cylinder is an example of a cylinder in which the moving line follows a circular path. Other cylinders include rectangular cylinders, triangular cylinders and cylinders having undefined shape paths.

In addition to being circular cylinders, the reference tube 10 is nonconductive. Nonconductive means the material of which the reference tube 10 is made does not conduct electrical charge. Electrical charge can be conducted by electrons moving through the material of which the reference tube 10 is made, or by ions or electrons moving through interstices between the particles making up the reference tube. Liquid electrolyte in the pores of, for example, a clay pipe, would permit electrical conduction by electrons being conducted through the electrolyte in the pores and ions flowing through the pores. However, the preferably plastic reference tube 10 does not permit electrical conduction by either mechanism or any other mechanism.

Bare metal coupons 16 and 18 are mounted to the ends of the coupon tubes 12 and 14, respectively. Electrically insulated conductors 20 and 22 extend from attachment to the coupons 16 and 18, through the coupon tubes 12 and 14, respectively. The coupon tubes 12 and 14 protect the conductors 20 and 22 during installation of the test station 8. The preferred coupons 16 and 18 are rods. A rod is defined as an elongated, solid body and includes, for example, cylinders, cones, parallelepipeds, and ellipsoids. The preferred coupons 16 and 18 are circular cylindrical rods, which minimizes any shielding of current by, or from, the coupons. Both coupons in any test station preferably have the same or about the same surface area exposed to the electrolyte, and most preferably are essentially identical in shape and size. For example, in an experiment performed with the present invention, a coupon size referred to as "standard" was established for the experiment as 1.4 square inches (9 square centimeters) and a coupon size referred to as "large" was established at 7.8 square inches (50 square centimeters). Both coupons in each test station were either standard or large. If the coupon which measures off-potential is rendered unusable, the coupon which measures free corrosion potential can be used to perform the measurement the failed coupon performed by merely changing connections. This coupon arrangement provides for uniform current distribution.

The coupons 16 and 18 protrude from the reference tube 10 a minimal distance to minimize, and preferably eliminate, the IR drop. The distance is preferably about ¼ to about ½ inch of the coupon protruding beyond the end 28 of the reference tube 10.

At the second end 30 of the reference tube 10, a cap 23 is shown in phantom. The cap 23 attaches to the reference tube 10 in a conventional manner and houses connectors. Typical devices within the chamber 27 could include a conventional voltage sensor, such as a voltage meter, which takes measurements during operation of the test station.

Figure 3:
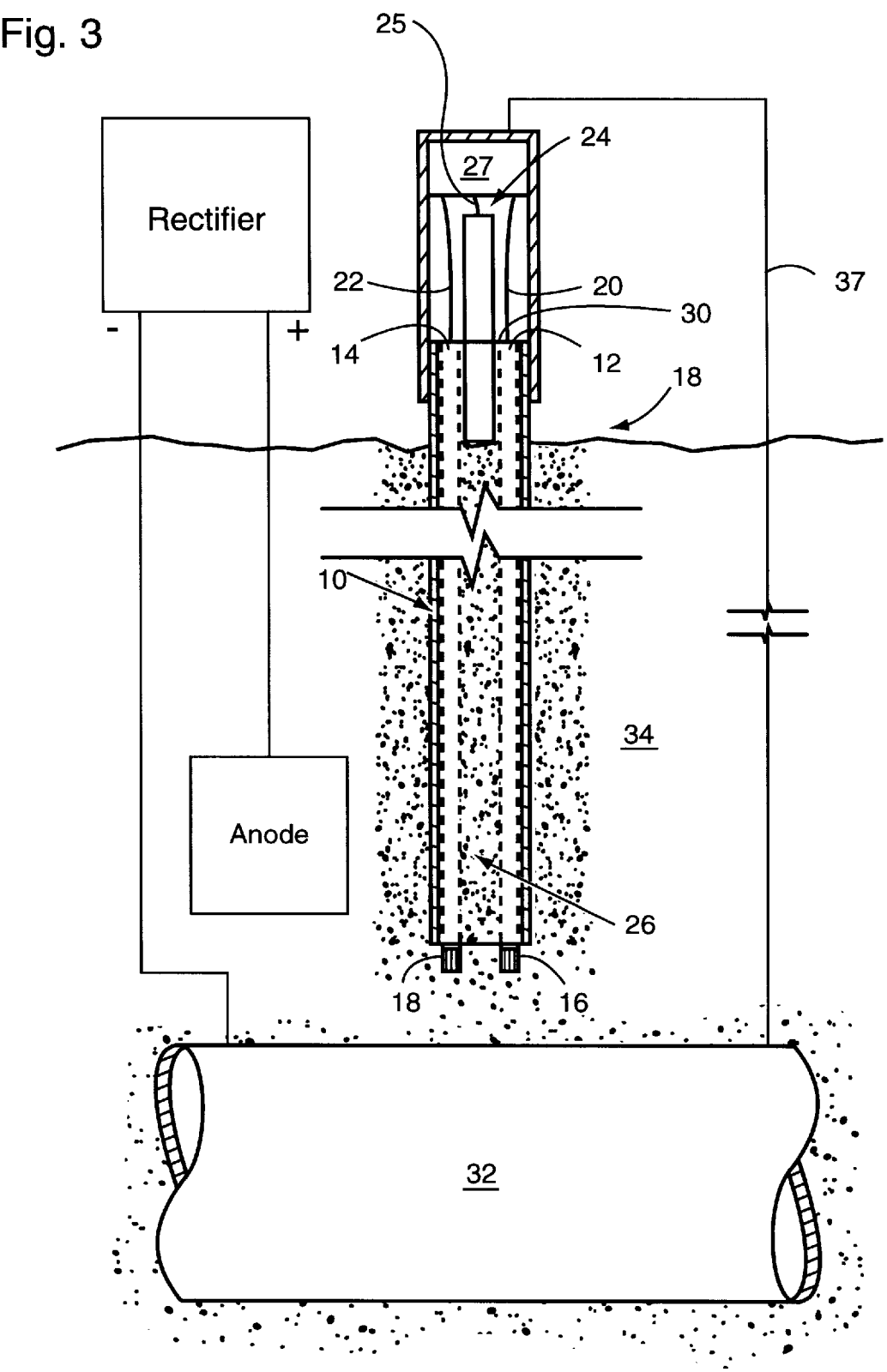
FIG. 3 is a side view illustrating the preferred embodiment of the present invention in its operable position mounted within the ground and in close proximity to a pipe.
Figure 8:
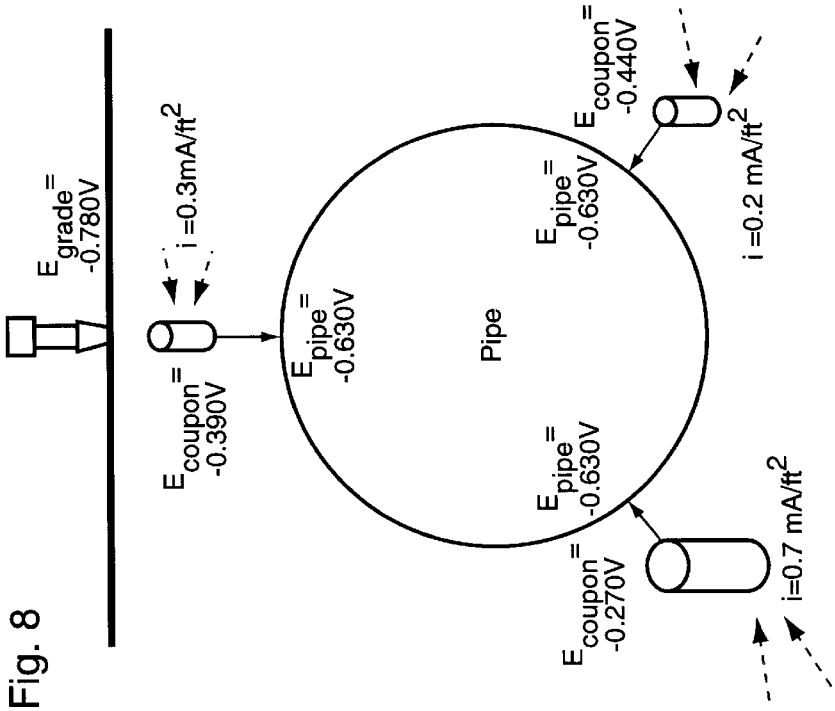
Figure 7:
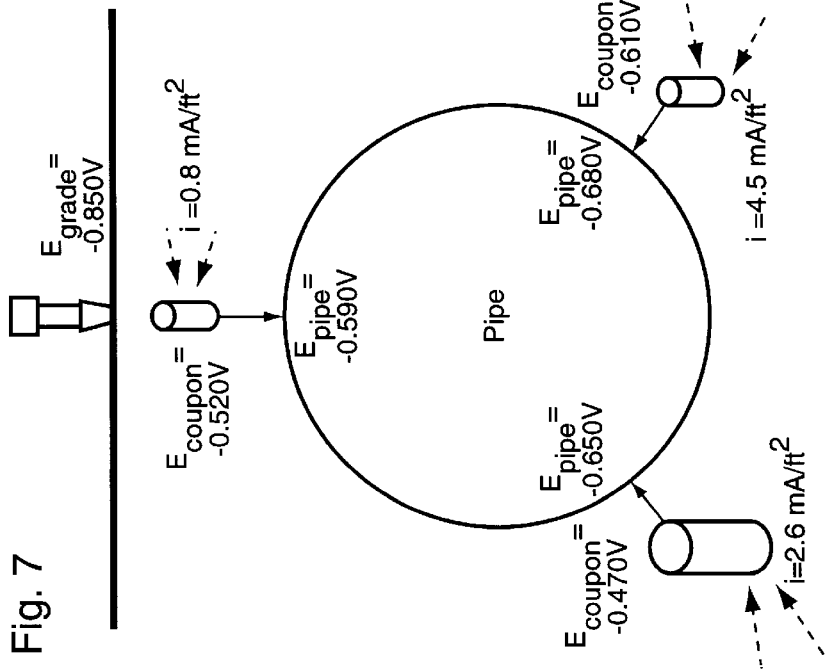
Figure 12:
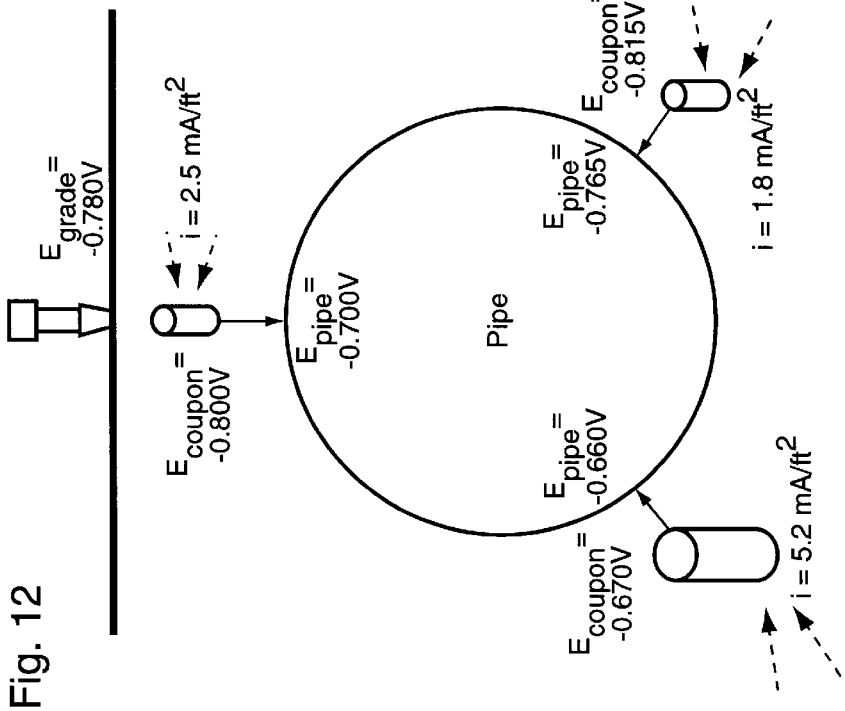
Figure 11:
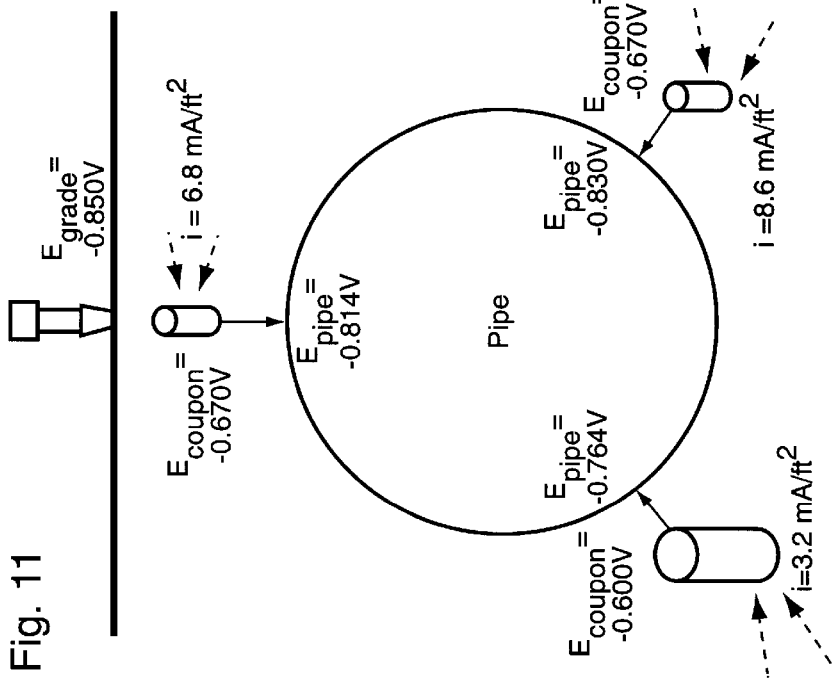
Figure 14:
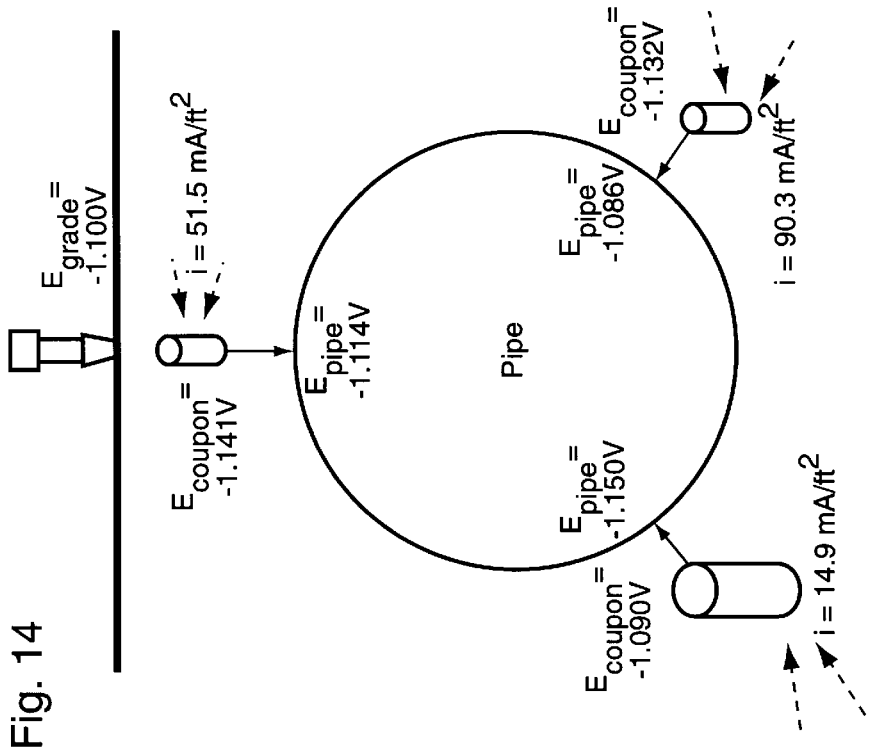
Figure 13:
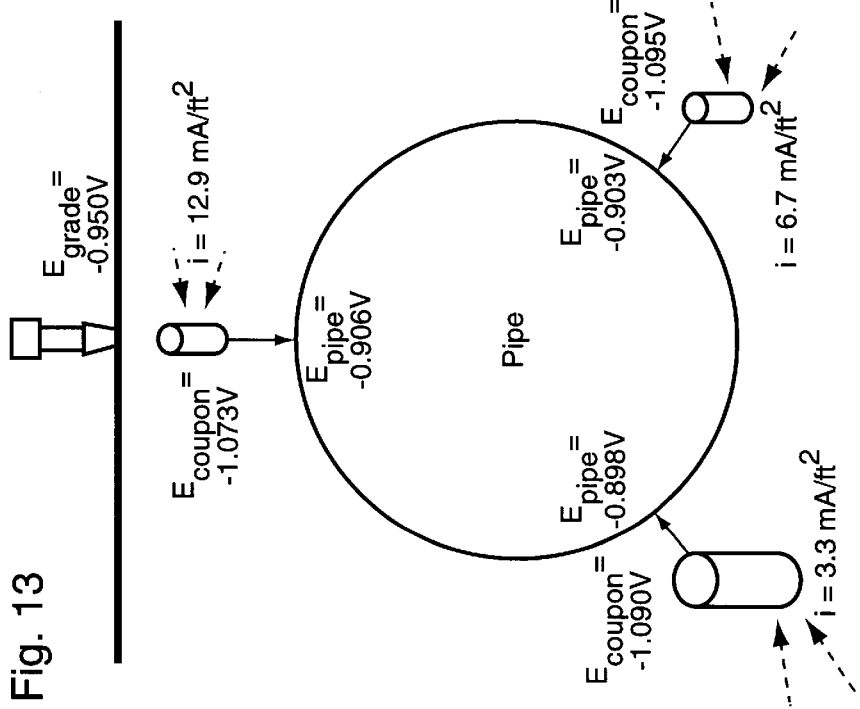
Figure 16:
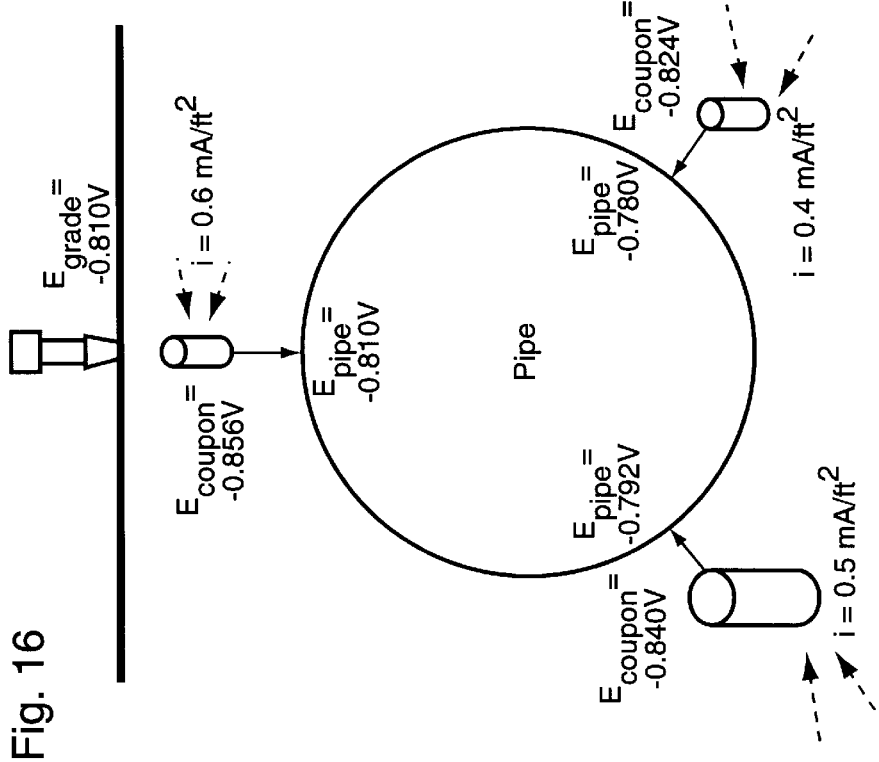
Figure 15:
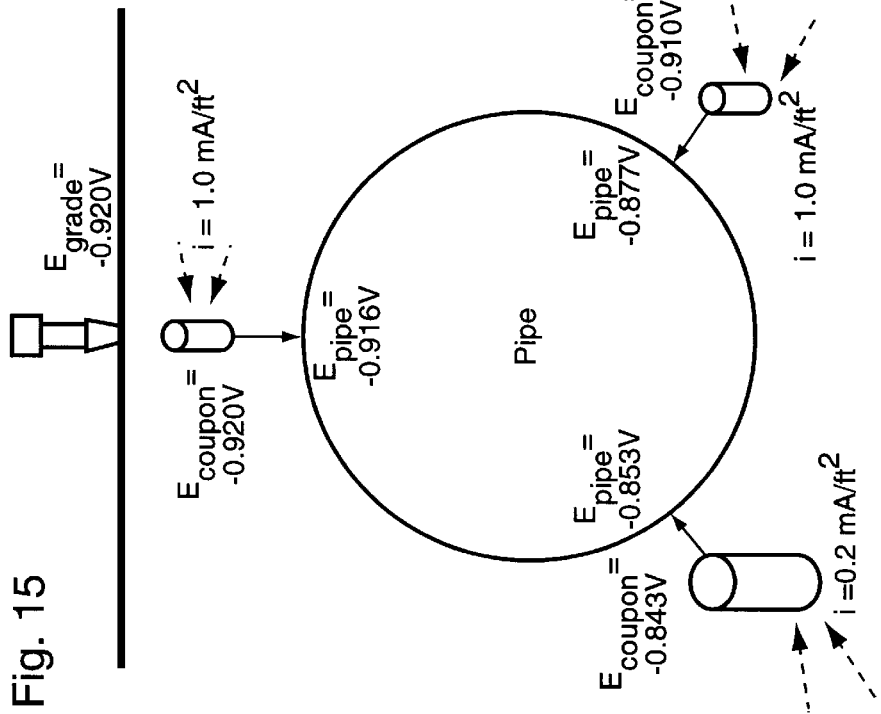
Figure 17:
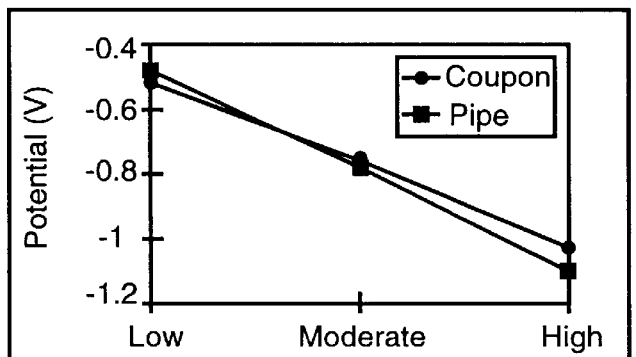
FIGS. 17 through 28 illustrate graphically the coupon potentials versus the pipe potentials for the test site.
Figure 18:
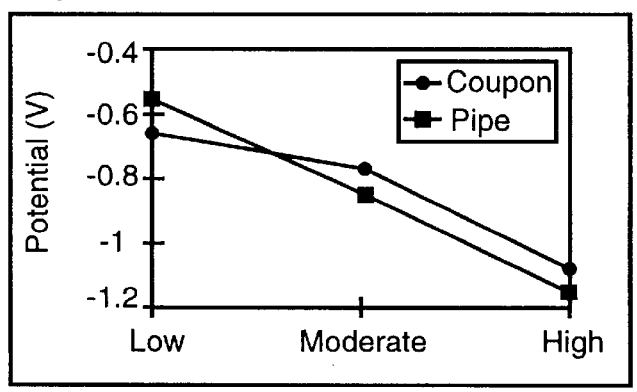
Figure 19:
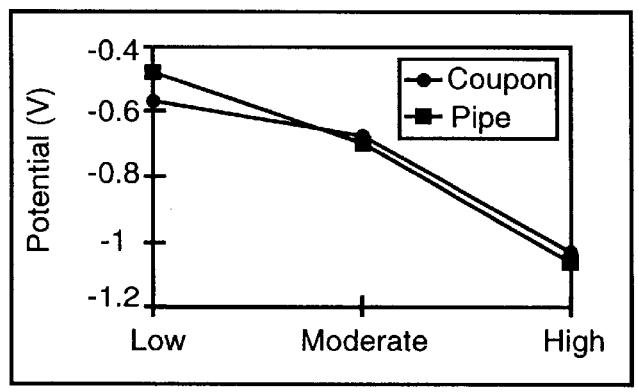
Figure 20:
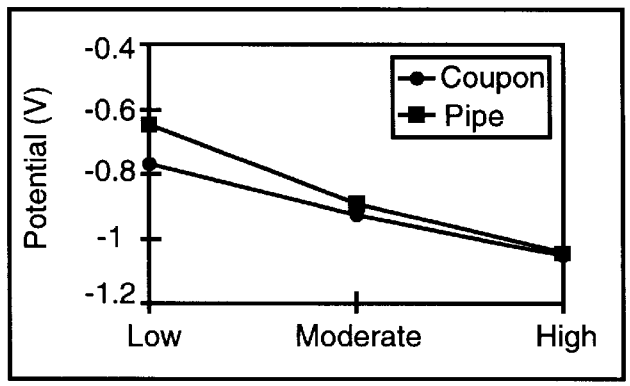
Figure 21:
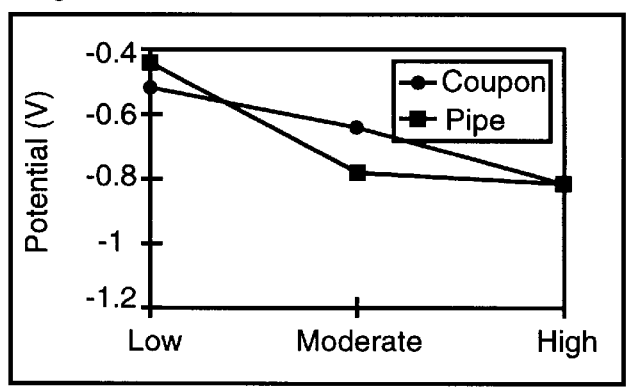
Figure 22:
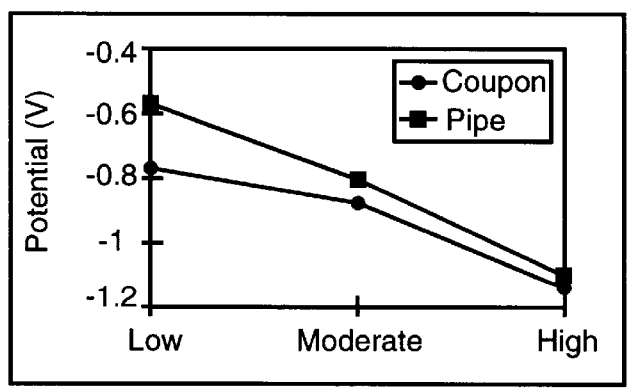
Figure 23:
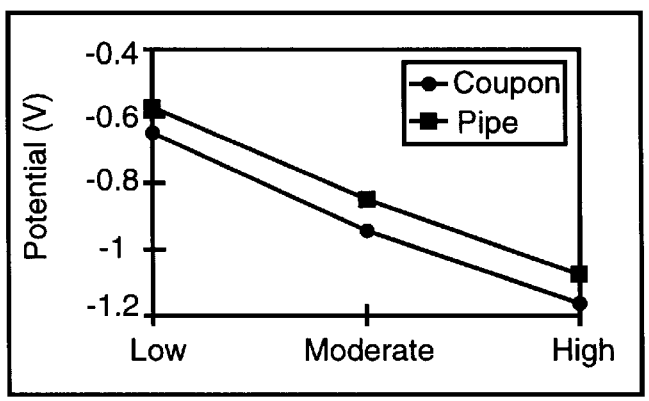
Figure 24:
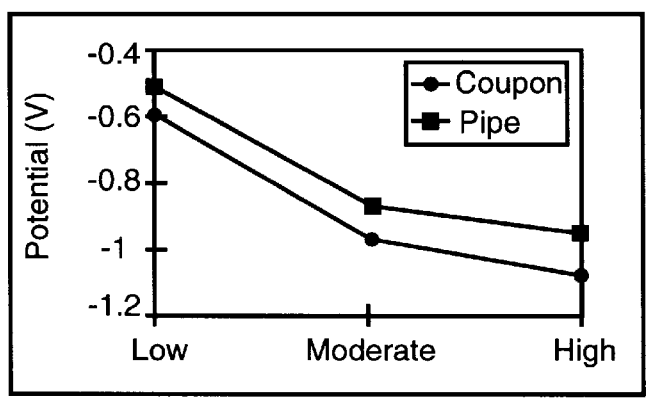
Figure 25:
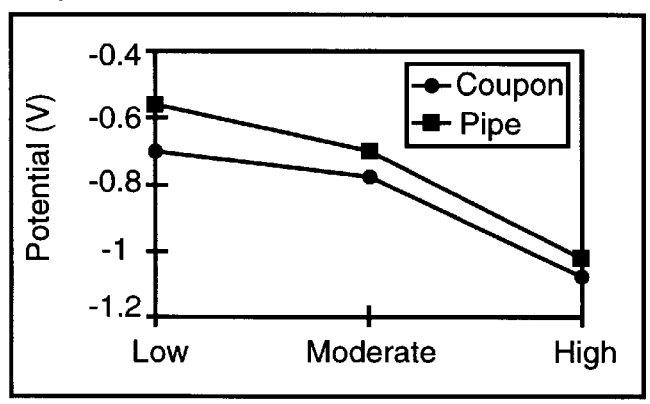
Figure 26:
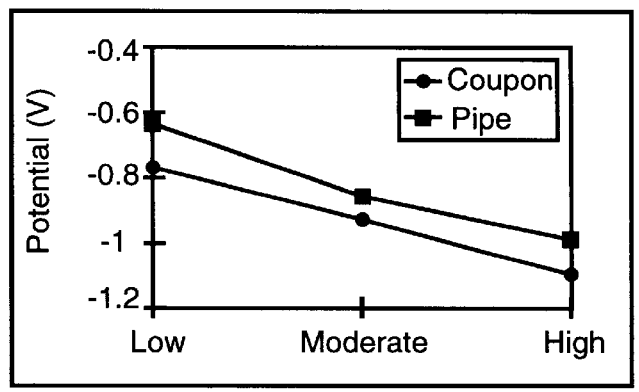
Figure 27:
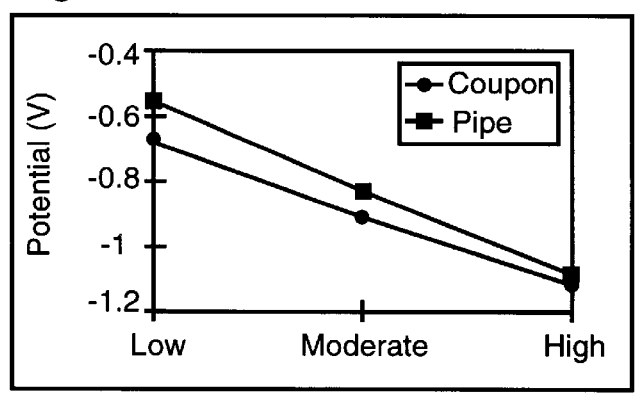
Figure 28:
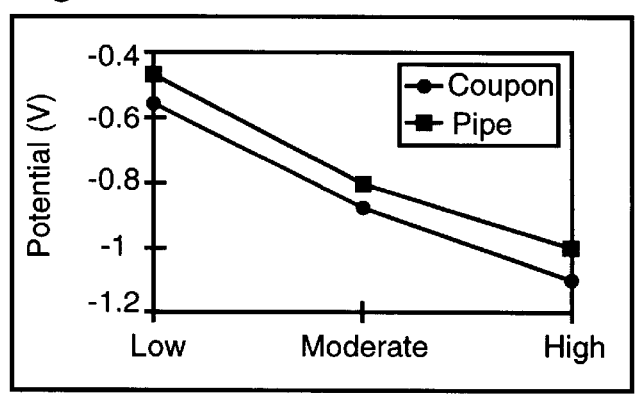

Referring to FIG. 3, the preferred test station 8 is shown in its operable position with its lower end submerged in the earth, in close proximity to a buried metal pipe 32. The test station 8 is preferably placed in the position shown in FIG. 3 by augering a 3 inch diameter hole into the soil 34 near the pipe 32 until the lower end of the hole is within four to eight inches of the pipe 32. Soil can include sand, gravel and other particulate materials which coat the earth. The reference tube 10 is extended downwardly into the hole, and the coupons 16 and 18, which have substantially the same metallurgical attributes as the pipe 32, are inserted into the soil at the bottom of the hole. By placing the coupons 16 and 18 in the minimally disturbed soil near the pipe 32, the coupons 16 and 18 are in an environment which simulates that of the pipe 32.

The reference tube 10 protrudes from the ground 34, and any excess can be merely cut off to limit the protruding amount to a specific height. The conductors extend from the coupons 16 and 18 up through the coupon tubes 12 and 14, which initially extend only part of the length of the reference tube 10 from the coupons toward the reference tube end 30. The conductors are merely tucked downwardly into the reference tube 10 below the cutoff point, and the reference tube 10 is cut off. The remaining lengths of the coupon tubes 12 and 14 are cut to fit flush with the reference tube end 30. The conductors are extended through the coupon tubes 12 and 14. The soil removed during augering is then backfilled (poured and compressed) into the interior of the reference tube 10 to the original grade level to approximate its original conditions. The coupon tubes 12 and 14 protect the conductors 20 and 22 during backfilling of the reference tube 10.

A reference electrode 24, which is preferably a 4 conventional copper/copper sulfate half cell, is placed in the upper end 30 of the reference tube 10 in contact with the soil 26 within the reference tube 10. The reference electrode 24 could, of course, be extended downwardly into the reference tube 10 closer to the coupons 16 and 18 by merely replacing less of the soil 26 in the reference tube 10 after augering. However, it is preferred to fill the reference tube 10 back to ground level and place the reference electrode 24 on the upper surface of the soil. The first coupon conductor 20, the second coupon conductor 22, and a reference electrode conductor 25 are all connected to appropriate connections in the chamber 27 of the cap 23.

The conductor 37 electrically connects the first coupon 16 to the pipe 32. This connection gives the coupon 16 the same cathodic protection as the pipe 32. As current flows through the conductor 37, it can be measured by conventional means. It is the connection between the pipe 32 and the first coupon 16 that is interrupted to measure the off-potential of the first coupon 16.

FIG. 4 illustrates three possible positions of coupons on a test station with respect to a pipe 50. Three test stations 44, 46 and 48 are shown installed at three possible positions. The test stations 44, 46 and 48 were arranged in the experiment referred to above at similar positions to those shown in FIG. 4, but each test station was linearly spaced along the length of the pipe 50. The test stations 44 and 48 are on opposite sides of the pipe 50 spaced along the pipe 50 length, and at the same depth, so that the coupons which are part of the lower test stations 44 and 48 experience the same effects of depth. The left test station 48 has large coupons, and the right test station 44 has standard coupons. This permits study of the effect of surface area on the coupons. The upper test station 46, having standard coupons attached to it, is mounted directly above the pipe 50, which, in comparison to the deeper test stations 44 and 48, permits study of the effect of depth or circumferential position on the coupons.

In the experiment performed, data were obtained for three field sites and one test site. The first field site was in Victorville, Calif., the second field site was in Elkins, W. Va., and the third field site was in Greenup, Ky. A test site was constructed in Sugar Grove, Ohio in which a single test station was placed near a bare pipe and two test stations were positioned near each of a poorly coated and a well coated pipe. In this experimental study, the on and off potentials for the pipe and the coupons were measured, the coupon currents were measured, and the depolarization of the pipe and the coupons was measured. The coupon and pipe off-potentials and the coupon currents are shown in the illustrations of FIGS. 5–16.

The structural features of the preferred test station 8 provide advantages. Both coupons 16 and 18 in the test station 8 protrude the same distance from the reference tube 10, and therefore they extend into the ground 34 to the same depth when the test station 8 is installed as shown in FIG. 3. This causes the coupons 16 and 18 to be exposed to similar environments to each other and the pipe.

Because the reference tube 10 is made of a non-conductive material, little or no currents affect the potential measured between the reference electrode 24 and the coupons 16 and 18. The coupons 16 and 18 are able to be placed within 0.5 inches of the nonconductive reference tube 10, and therefore the IR drop in the coupon to soil potential measurement is minimized further. Additionally, because the coupons 16 and 18 are positioned on opposite sides of the reference tube 10, the reference electrode 24 is equidistant from both coupons when it is positioned in its preferred operable position. Therefore, any IR drop will be similar for each coupon.

The reference tube 10 and the coupon tubes 12 and 14 are made of relatively inexpensive plastic pipe in the preferred embodiment. After the test station is placed in the soil, the protruding portion may be cut off to leave the exposed test station height that is desired. Because of the simplicity of the structure, the inexpensive materials used, and the fact that no destruction of essential parts will occur in the process, the excess portion of the protruding test station is simply severed and discarded. After such removal of excess test station, electrical connections are made to the connectors or monitoring devices, the coupons and a reference electrode. This permits the preferred embodiment to be made as small as is desired.

While certain preferred embodiments of the present invention have been disclosed in detail, it is to be understood that various modifications may be adopted without departing from the spirit of the invention or scope of the following claims.

We claim:

1. A test station for measuring the effectiveness of cathodic protection provided by a cathodic protection system for mitigating the corrosion of a metal structure immersed in an electrolyte, the test station comprising:

(a) a nonconductive reference tube having first and second opposite reference tube ends, and a sidewall surrounding and defining an interior, elongated chamber;

(b) first and second spaced coupon tubes mounted to the sidewall of the reference tube within the chamber, each coupon tube having a sidewall terminating in a coupon tube end near the first reference tube end;

(c) a first coupon of substantially the same metal as the immersed structure, said coupon being mounted to said end of the first coupon tube and having an attached electrically insulated conductor extending from the coupon through the first coupon tube for connecting to the immersed structure; and (d) a second coupon of substantially the same metal as the immersed structure, said coupon being mounted to said end of the second coupon tube and having an attached electrically insulated conductor extending from the coupon through the second coupon tube.

2. A test station in accordance with claim 1, wherein the coupons are rods.

3. A test station in accordance with claim 1, wherein each coupon has a circular cylindrical sidewall and at least one planar end wall.

4. A test station in accordance with claim 3, wherein the surface area of the first coupon is about equal to the surface area of the second coupon.

5. A test station in accordance with claim 1, wherein the reference tube is a circular cylindrical plastic tube about three inches in diameter, and the coupon tubes are circular cylindrical plastic tubes.

6. A test station in accordance with claim 1, wherein the coupon tubes are mounted to the sidewall of the reference tube at about 180 degree intervals from each other.

7. A test station in accordance with claim 6, further comprising a reference electrode positioned in the reference tube equidistant from each coupon.

8. A test station in accordance with claim 7, further comprising a voltage meter connected to the first coupon and the reference electrode for measuring an off-potential at the first coupon.

9. A test station in accordance with claim 7, further comprising a voltage meter connected to the reference electrode and at least one of the coupons for measuring an off-potential at the first coupon and a free corrosion potential at the second coupon.

10. A test station in accordance with claim 1, further comprising a voltage meter connected to a reference electrode and at least one of the coupons for measuring an off-potential at the first coupon and a free corrosion potential at the second coupon.

11. A test station in accordance with claim 1, wherein each coupon protrudes less than about one-half inch from the first end of the reference tube.

12. A method of measuring the effectiveness of cathodic protection provided by a cathodic protection system for mitigating the corrosion of a metal structure buried in soil, the method comprising:

(a) removing soil to form a hole having a floor of substantially undisturbed soil;

(b) inserting into said hole a test station, including a nonconductive reference tube having first and second opposite reference tube ends, and a sidewall surrounding and defining an interior, elongated chamber, first and second spaced coupon tubes mounted to the sidewall of the reference tube within the chamber, each coupon tube having a sidewall terminating in a coupon tube end near the first reference tube end, a first coupon mounted to the end of said first coupon tube, and a second coupon mounted to the end of the second coupon tube;

(c) extending the coupons into the soil at the hole floor;

(d) backfilling soil into the chamber of the reference tube;

(e) positioning a reference electrode at least partially in the reference tube chamber;

(f) electrically connecting the first coupon to the buried structure;

(g) connecting a voltage sensor to the reference electrode and the first coupon; and (h) measuring the off-potential of the first coupon after electrically disconnecting the first coupon from the buried structure.

13. A method in accordance with claim 12, further comprising connecting the voltage sensor to the second coupon and the reference electrode and measuring the free corrosion potential at the second coupon.

* * * * *